United States Patent
Bruder et al.

(10) Patent No.: US 6,909,769 B2
(45) Date of Patent: Jun. 21, 2005

(54) METHOD AND APPARATUS FOR THREE-DIMENSIONAL IMAGING OF A MOVING EXAMINATION SUBJECT, PARTICULARLY FOR HEART IMAGING

(75) Inventors: Herbert Bruder, Hoechstadt (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/126,049

(22) Filed: Apr. 19, 2002

(65) Prior Publication Data

US 2002/0181645 A1 Dec. 5, 2002

(30) Foreign Application Priority Data

Apr. 19, 2001 (DE) .......................... 101 19 228

(51) Int. Cl.[7] .............. A61B 6/00; H05G 1/60
(52) U.S. Cl. .............. 378/8; 378/95; 378/197; 378/207; 600/428; 600/431
(58) Field of Search .................. 378/8, 95, 196, 378/197, 198, 207; 600/428, 431; 424/94

(56) References Cited

U.S. PATENT DOCUMENTS

| | | | | |
|---|---|---|---|---|
| 5,262,946 A | * | 11/1993 | Heuscher | 378/15 |
| 5,446,799 A | * | 8/1995 | Tuy | 382/132 |
| 5,515,416 A | * | 5/1996 | Siczek et al. | 378/197 |
| 6,120,180 A | * | 9/2000 | Graumann | 378/206 |
| 6,139,183 A | * | 10/2000 | Graumann | 378/206 |
| 6,154,516 A | * | 11/2000 | Heuscher et al. | 378/15 |
| 6,243,437 B1 | * | 6/2001 | Hu et al. | 378/8 |
| 6,275,560 B1 | * | 8/2001 | Blake et al. | 378/8 |
| 6,324,254 B1 | * | 11/2001 | Pflaum | 378/95 |
| 6,370,217 B1 | * | 4/2002 | Hu et al. | 378/8 |
| 6,379,041 B1 | * | 4/2002 | Schuetz et al. | 378/205 |
| 6,381,487 B1 | * | 4/2002 | Flohr et al. | 600/425 |
| 6,382,835 B2 | * | 5/2002 | Graumann et al. | 378/198 |
| 6,393,091 B1 | * | 5/2002 | Slack et al. | 378/8 |
| 6,466,638 B1 | * | 10/2002 | Silver et al. | 378/4 |
| 6,470,208 B1 | * | 10/2002 | Woodford et al. | 600/428 |
| 6,491,430 B1 | * | 12/2002 | Seissler | 378/207 |
| 6,510,337 B1 | * | 1/2003 | Heuscher et al. | 600/428 |
| 2002/0126794 A1 | * | 9/2002 | Rasche et al. | 378/8 |

* cited by examiner

Primary Examiner—Allen C. Ho
(74) Attorney, Agent, or Firm—Schiff & Hardin LLP

(57) ABSTRACT

In a method and apparatus for three-dimensional imaging of a moving examination subject, particularly heart imaging with an examination apparatus having at least one C-arm with a radiation source and a radiation receiver, the C-arm rotates around the examination subject at least once through 180° plus the radiation fan angle during the time span in which a contrast agent is in the examination subject for the registration of the two-dimensional projection images, on the basis of which a three-dimensional image reconstruction ensues.

26 Claims, 3 Drawing Sheets

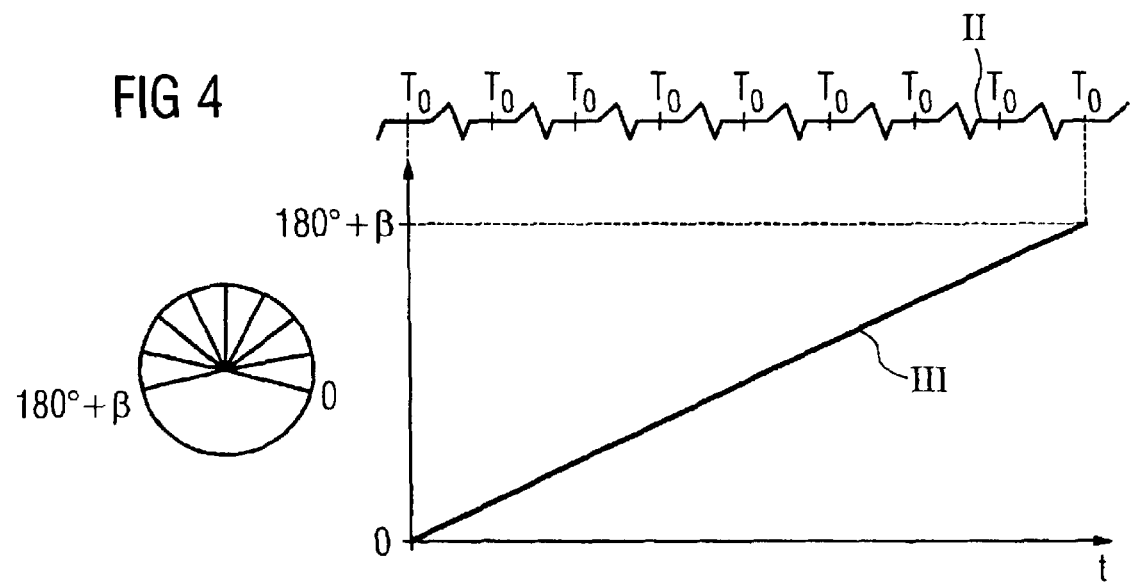

METHOD AND APPARATUS FOR THREE-DIMENSIONAL IMAGING OF A MOVING EXAMINATION SUBJECT, PARTICULARLY FOR HEART IMAGING

BACKGROUND OF THE INVENTION

1. Field of the Invention

The present invention is directed to a method for three-dimensional imaging of a moving examination subject, particularly heart imaging with an examination apparatus having at least one C-arm with a radiation source and a radiation receiver.

2. Description of the Prior Art

A standard application for an examination apparatus or angiography system of the C-arm type is the registration of projection images from one or from a few different directions. Usually, the exposures are produced as two-dimensional projection images and are viewed as such. Three-dimensional reconstructions of the examination region for presenting a three-dimensional angiography image are used only in interventional imaging for treating diseases of the vascular system in the brain on the basis of the two-dimensional projection images that have been registered. The known possibilities, however, only allow the examination and three-dimensional presentation of examination regions from which adequate data has been obtained. It would be desirable in heart imaging to be able to produce three-dimensional presentations of the heart in different phases in order, in particular to be able to investigate the coronary vessels in this way. This is currently not possible, however, because too few projection images for the same heart phase can be registered with the examination apparatus within the extremely short time during which the added contrast agent required for the registration of the projection image is located in the examination region. The usual contrast agent dwell time in the examination region, i.e. for example the coronary vessels, amounts to only approximately two seconds. Given a standard rotational speed of the C-arm of 20°/s and assumed pulse of 60, i.e. a heart frequency of 1 Hz, this means that only two projections from different angles can be obtained at the same heart phase and are available for the 3D reconstruction. Thus no diagnostic three-dimensional presentation can be reconstructed.

SUMMARY OF THE INVENTION

An object of the present invention is to provide a method and apparatus for three-dimensional imaging of a moving examination subject, i.e. for example, of the heart, that allow an adequately precise and diagnostically relevant, three-dimensional reconstruction of the examination region.

This object is achieved in accordance with the invention in a method and an apparatus of the type initially described wherein the C-arm rotates around the examination subject at least once through 180° plus the radiation fan angle during the time span in which a contrast agent is in the examination subject for the registration of the two-dimensional projection images, on the basis of which a three-dimensional image reconstruction ensues.

In accordance with the invention proposes that the C-arm rotates around the examination subject by a large angular range, namely by at least 180° plus the radiation fan angle, so that a complete dataset that enables the reconstruction can be theoretically acquired according to the reconstruction rules as known form computed tomography. This can be achieved by means of an adequately high rotational speed of the C-arm, whereby the C-arm should rotate with a speed of at least 30°/s. Higher rotational speeds of, for example, 60°/s or more, however, are desirable. Alternatively or additionally, this can also be achieved by a modified administration of the contrast agent. The contrast agent, which is usually arterially supplied since it is present in the coronary vessels immediately after administration in this case (differing from venous delivery where it initially proceeds into the lung and only then into the heart), should thereby be administered such that a dwell time of at least 4 s, particularly of at least 5 s, occurs in the examination region. Longer dwell times are likewise desirable, for example 6 or 7 seconds. By modifying the amount of contrast agent and/or the injection rate, noticeably longer dwell times of the contrast agent in the arteries and the ventricles thus can also be achieved, so that the C-arm can swivel back and forth several times given an adequately rotational speed and the angular range of 180° plus radiation fan angle can be multiply traversed. In addition, of course, there is the possibility of administering contrast agent twice or repeatedly in order to thus lengthen the dwell time. More heart cycles are covered during the contrast agent presence the longer the dwell time is, and more equiphase projections thus are obtained. Since, given a rotation through at least 180° plus the radiation fan angle, the examination region is transirradiated once from each direction, an adequately large dataset is present that allows a diagnostically relevant 3D reconstruction of the examination subject, i.e., for example of the coronary vessels and of the heart in different heart phases, and thus different positions.

The registration of the projection images should ensue during the movement of the C-arm around the examination subject with an image rate of at least twenty images/s, preferably at least 25 images/s. For example, given an assumed contrast agent dwell time of 6 s and an image rate of 25 images/s, 150 projections are obtained during the rotation of the C-arm, distributed over the angular range that has been scanned. The respective parameters may possibly lie below the indicated minimum limits as long as an adequately large number of projections is obtained during the contrast agent dwell time. The higher the image rate or the rotational velocity, the better.

In order to enable an exact allocation of the individual two-dimensional projection images the respective heart cycles and to respective heart phases therein, it has proven advantageous to register an ECG parallel to the registration of the images for enabling an allocation of a projection image to a motion phase of the examination subject, i.e. to the heart in this case. An ECG-triggered heart reconstruction ensues in this embodiment. The heart phase in which a specific projection was registered can be exactly identified on the basis of the ECG, this being advantageous for the selection of the relevant projections that are required in the framework of the 3D reconstruction dependent on the desired heart phase to be presented.

In another embodiment only projection images registered in the heart diastole are employed for the three-dimensional reconstruction. In this embodiment of the invention, advantageous use is made of the fact that the heart (ventricle, myocardial) wall moves only very little in the relatively long diastole, i.e. the quiescent phase of the heart. Given a duration of a heart beat of 800 ms through 1 s, the diastole or the quiescent phase amounts to approximately 500 ms. However, an evaluation of the systolic projections is also conceivable for specific examinations.

Two different methods are possible for the reconstruction following the image registration. In one embodiment of the invention, the projection images registered in the different heart motion cycles are employed for a motion phase defined in the ECG, with the projection images missing for a complete set of projection images required for the reconstruction being computationally determined by interpolation.

According to this embodiment of the invention, only those projections that were registered exactly at the respectively same heart phase within the several heart cycles that occurred during the scope of the registration are selected from the totality of all projection images. Since equiphase projections are not available for all angular positions, it is required that the projections missing for the complete dataset in addition to the projections measured for the given heart phase in the different heart cycles be supplemented by interpolation with respect to the respective angle.

In another embodiment all projections measured within a predetermined time span $\Delta T$ in a heart cycle are employed, with the projection images missing for a complete set of projection images required for the reconstruction being computationally determined by interpolation. Since the heart assumes a quasi-stationary condition in the diastole for the duration of the diastole, the projections registered in this time span $\Delta T$, all of which show essentially the same heart phase, can be employed. The intermediate angular ranges wherein no projections are present, because they lie outside the time span $\Delta T$, are filled by interpolation. Less interpolation is needed in this embodiment than in the embodiment described immediately preceding.

In a further embodiment, those projection images from the family of projection images that lie within a predetermined projection angular range, and whose time interval from the defined motion phase is minimal, are employed in the reconstruction for a motion phase defined in the ECG, and the overall rotational angle of the C-arm is subdivided into equidistant projection angle ranges, and the corresponding projection images are selected for each projection angle range.

In this embodiment of the invention, the reconstruction employs only registered projection images, and a computational interpolation thus does not ensue. Since, however, a projection image or projection images is/are not present for each projection angle range for the respectively desired heart phase, the corresponding projection angle range and the projections lying therein are employed that have the least time spacing from the desired heart phase, as defined in the ECG. The projections registered within the projection angle range are then utilized for the reconstruction.

Since these projection angle ranges or their projection images were generally not measured exactly with respect to the desired heart phase, a temporal unsharpness occurs in the transition between neighboring projection angle ranges. In order to avoid this unsharpness or motion-dependent unsteadiness in the projection image dataset, it is expedient for the projection angle ranges to overlap and to undertake a weighted superimposition.

In order to be able to take the mechanical instability of C-arm devices into consideration, the same methods from known 3D angiography reconstruction can be used that are employed for the presentation of stationary examination subjects such as, for example, the brain. For example, this can be online measurement with suitable markers (pose determination system) or a use of geometry data in the framework of the reconstruction that were acquired by calibration.

It is also advantageous to employ a biplanar C-arm, i.e. a C-arm system having two C-arms that usually reside orthogonally relative to one another, each thereof having a radiation source and a radiation receiver of any type (for example, an x-ray image intensifier or a solid-state detector).

DESCRIPTION OF THE DRAWINGS

FIG. 4 schematically illustrates a third reconstruction method in accordance with the invention.

DESCRIPTION OF THE PREFERRED EMBODIMENTS

Figure 1:
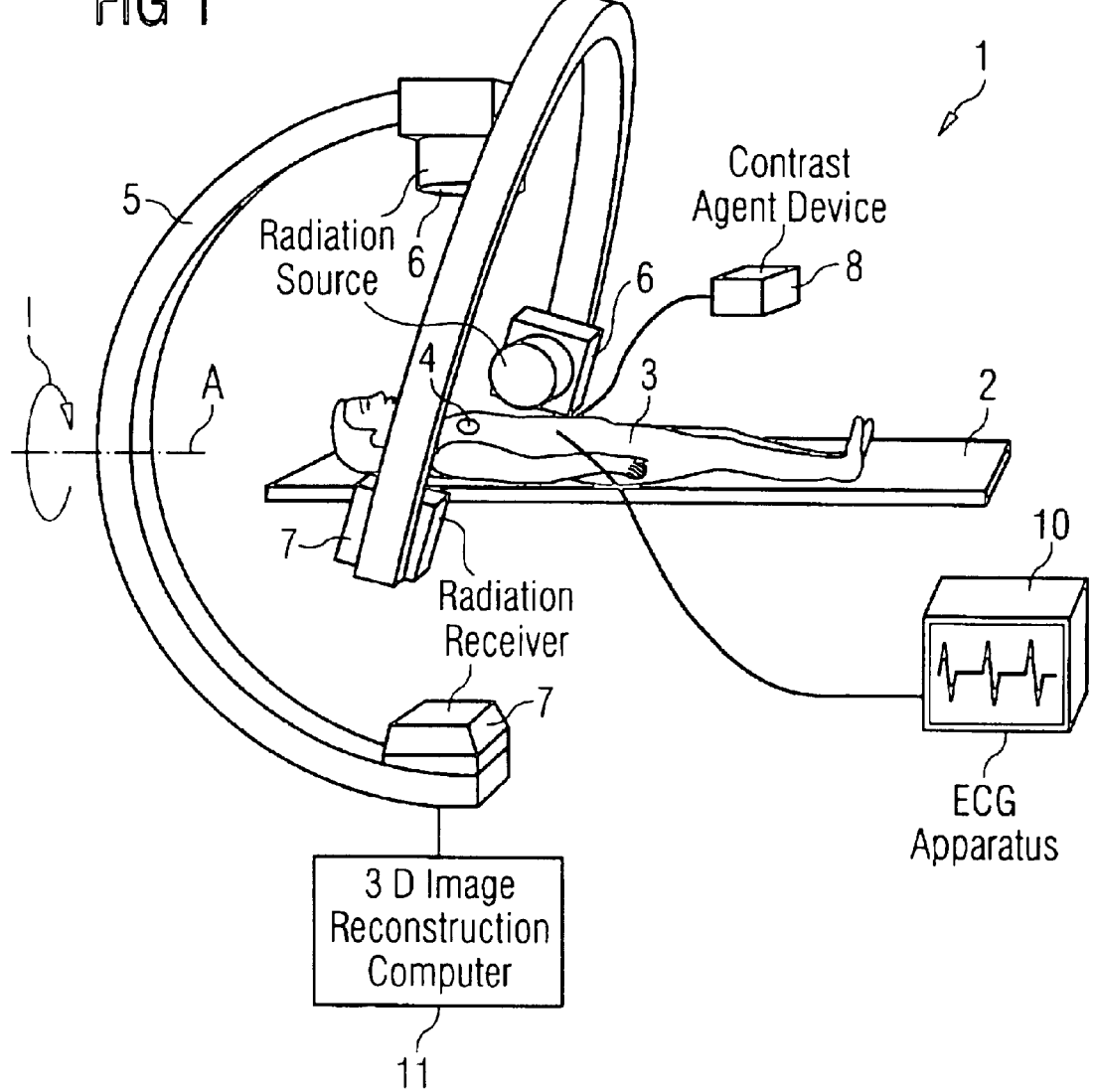
FIG. 1 is a schematic illustration of a medical examination apparatus for the implementation of the inventive method.

FIG. 1 shows an inventive medical examination apparatus 1 having a patient bed 2 on which a patient 3 whose heart 4 is to be examined lies in the illustrated exemplary embodiment. A C-arm 5 with a radiation source 6 and a radiation receiver 7 is provided for the examination, this being rotatable around the axis A, as indicated by the arrow 1. The radiation source 6 and the radiation receiver 7 thus rotate around the examination region, i.e. around the heart 4 in this case.

Contrast agent is administered to the patient with a contrast agent device 8 via a contrast agent line 9. This contrast agent is preferably arterially administered, so that it is already in the region of the heart 4 immediately after having been administered and is still present in adequate concentration. Further an ECG apparatus 10 is provided with which a ECG can be registered.

For the examination, the C-arm 5 rotates around the axis A during the time wherein the contrast agent is in the examination region. The rotational speed of the C-arm 5 as well as the delivery of the contrast agent is set such that the C-arm 5 rotates around the heart 4 during the presence of the contrast agent through at least 180° plus the radiation fan angle, i.e. the fan angle exhibited by the x-ray beam proceeding from the radiation source 6 to the radiation receiver 7. The rotational angle 180° plus the radiation fan angle is the minimum rotational angle that must be covered as long as the contrast agent is in the examination region so that a complete projection image dataset is present on whose basis a 3D reconstruction can ensue in a computer 11. Of course, it is also possible to multiply scan the angular range of 180° and fan angle by rotating the C-arm 5 back and forth with a suitable selection of the rotational speed and contrast agent administration, and thus to register an extremely great number of projections or a number of projection sets. The employment of a biplanar C-arm is also expedient, i.e. a system having two C-arms residing orthogonally relative to one another and each of which carries a radiation source and a radiation receiver and that, consequently, respectively scan twice the angular range.

Images are registered continuously during the rotation with an optimally high image rate. The image rate should amount to at least 20, preferably 25 images/s or more.

The following parameters selected as an example form the basis for the example explained below:

| | |
|---|---|
| Rotational speed of the C-arm: | 40°/s |
| Contrast agent dwell time: | 6s |
| Image rate: | 25 images/s |

Given a rotational speed of 40°/s and a contrast agent dwell time of 6 s, the C-arm 5 rotates by a total of 240° during the contrast agent dwell time. This essentially corresponds to 180° plus the radiation fan angle. Given an image rate of 25 images/s, a total of 150 projections images are obtained within this angular range. Given an assumed heart frequency of 1 Hz, thus, 25 projections are available per heart cycle. The time resolution can thus amount to up to 40 ms (1 s/125).

With the given heart frequency and the dwell time of the contrast agent, a total of six projections from six different angles are available for the reconstruction of a heart phase (i.e. of a point in time or time span during a heart period wherein the heart is quasi at rest). When a biplanar C-arm is employed, then a total of 12 projections are available.

The reconstruction also makes use of the fact that the heart (ventricle, myocardial wall) moves only very slightly in the relative long diastole (approximately half the heart cycle). Given an assumed heart frequency of 1 Hz, consequently, the diastole amounts to approximately 500 ms, and then approximately 12 projections are available per heart cycle in diastole. Given six heart cycles (6 second contrast agent dwell time), thus, approximately 72 projections from different angles.

These projections are now employed for the three-dimensional reconstruction of the heart.

Figure 2:
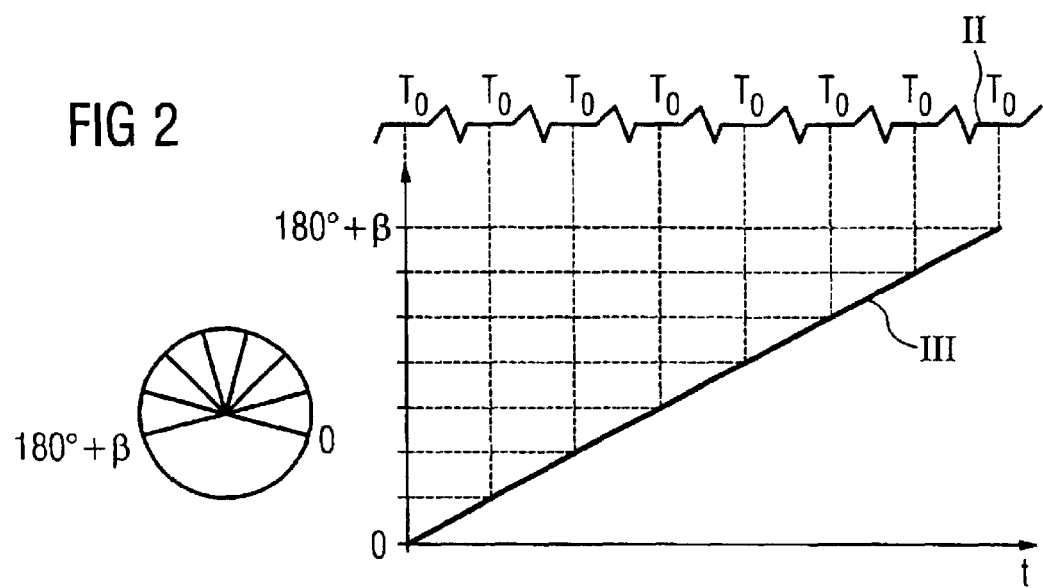
FIG. 2 schematically illustrates a first reconstruction method in accordance with the invention.

FIG. 2 shows a reconstruction method of a first embodiment in the form of a schematic illustration.

At the left in FIG. 2 the reconstruction volume is shown that must be filled with projections in the angular range 0°–180° plus β (β=radiation fan angle). The curve of the ECG is shown at the upper right on the basis of curve II. The respective projection angle is entered in the diagram lying therebelow along the ordinate over time as the abscissa. Since, given a rotation of the C-arm 5 by 180° plus the radiation fan angle, the heart is transirradiated once from every direction, the illustrated delta curve III derives.

A specific heart phase was selected for presentation within the ECG curve II, this lying in the point in time $T_0$. The ECG curve II as well as the curve III are allocated to one another in a time-related manner, so that the projections that were registered at the respective points in time can be allocated to specific heart phases.

In the illustrated exemplary embodiment, a total of six heart cycles were registered during the revolution of the C-arm 5. There is a heart phase $T_0$ to be presented within each heart cycle and there is a specific projection for this heart phase $T_0$. This total of six projections here lies at specific angles, as shown in the projection image volume illustrated at the left.

All of these six projections were measured exactly at the same heart phase $T_0$. The further projections required for the reconstruction that are required for the formation of a complete projection image set required for the reconstruction and that are still missing in the volume shown in FIG. 2 are generated by interpolation according to this reconstruction method, i.e. they are computationally determined. This reconstruction method thus is based on equiphase projections; missing projections are determined by interpolation.

Figure 3:
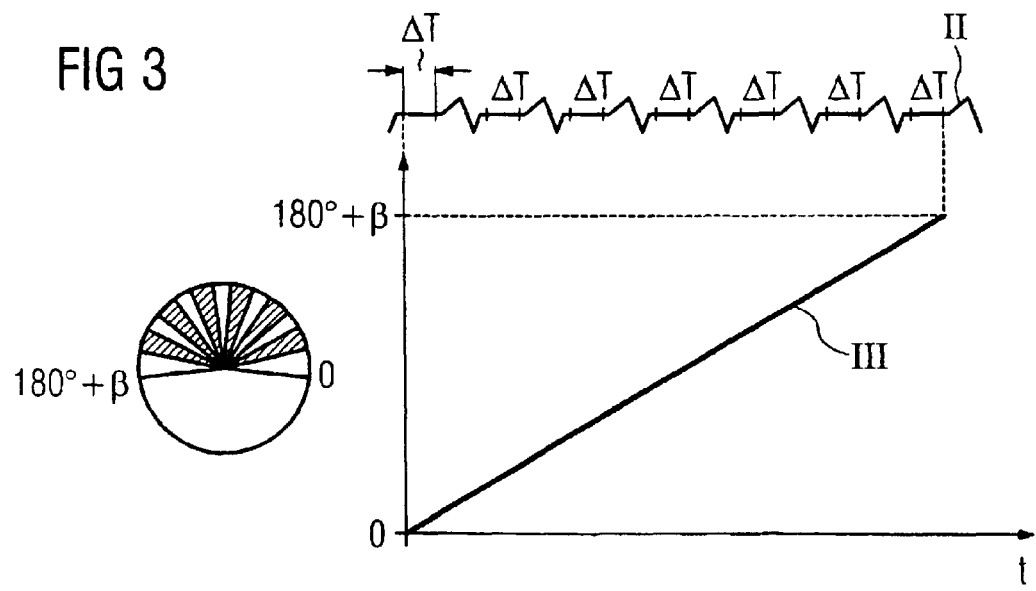
FIG. 3 schematically illustrates a second reconstruction method in accordance with the invention.

FIG. 3 shows a second alternative of the invention. Here, a time span ΔT that lies in the diastole and largely corresponds to the duration of the diastole. The heart is quasi-stable during the diastole, i.e. it is at rest and hardly changes in shape or, respectively, phase. All projections registered during the time span ΔT that show the heart—since it is essentially at rest—in the same phase from different projection angles are now employed for the reconstruction. The projections registered during a heart cycle within ΔT lie within a specific angular range; the respective angular ranges or their projections are transferred into the projection volume. The intermediate angular ranges that lie between the angular ranges and are not filled with registered projections are interpolated for reconstruction. Interpolation is carried out over a smaller angular range given this version of the method than given the procedure described with respect to FIG. 2.

FIG. 4 shows a second reconstruction method. In this embodiment, the reconstruction volume method is filled on the basis of equidistant projection angle ranges whose time interval is minimum from the desired heart phase. The desired heart phase is again referenced $T_0$. A projection angle range amounts, for example, to 30°. When, for example, the projection image volume is to be filled with projections relating to the projection angle range 0° through 30°, then those projections are selected from the entire projection image family that will register within the angular range 0° through 30° and that lie closest in time to the desired heart phase $T_0$. The second projection angle range 30° through 60°, etc., is correspondingly filled. It is expedient when the projection angle ranges overlap one another in order to avoid unsharpness and unsteadiness at the transition regions. Care must be exercised to insure that the angular ranges are always selected such that they lie within the diastole since projection images that were registered in the systole i.e. the work phase of the heart, should not be utilized for the reconstruction. Further, the time resolution is better as the regions are made finer.

It should be noted that the parameters cited for the described examples are only exemplary. The image rate can be higher or lower; the rotational speed of the C-arm 5 also can be higher or lower. It must merely be assured that the indicated angular range of 180° plus the fan angle can be covered within the contrast agent dwell time. In addition to an arterial contrast agent administration, which is preferred in order to achieve a high image contrast, a venous administration is also conceivable, but a noticeably long dwell time is established with this type of administration from the outset insofar as an adequate contrast agent concentration is achieved for an adequate image contrast.

Although modifications and changes may be suggested by those skilled in the art, it is in the intention of the inventors to embody within the patent warranted hereon all changes and modifications as reasonably and properly come within the scope of their contribution to the art.

We claim as our invention:

1. A method for three-dimensional imaging of a moving examination subject comprising the steps of:

injecting a contrast agent into a subject, said contrast agent having a dwell time in an examination region of said subject exhibiting substantially periodic movement;

mounting an x-ray source, which emits an x-ray fan beam having a fan angle, and a radiation detector on a C-arm, which exhibits mechanical instability at high rotational speeds, and rotating said C-arm and said x-ray source and said radiation detector around said examination region at least once through 180° plus said fan angle during said dwell time at a high speed for obtaining data during said dwell time representing a sufficient number of two-dimensional projections of said examination region to allow reconstruction of a three-dimensional image that is substantially free of artifacts due to said movement, said x-ray source and said radiation detector, due to said mechanical instability at said high speed, having respectively different geometric relations in different projections;

recording anew the geometric relations of said x-ray source, said radiation detector and said subject for each of said projections as each of said projections is obtained; and reconstructing said three-dimensional image from said data and making said three-dimensional image free of said artifacts by using said recorded geometric relations.

2. A method as claimed in claim 1 comprising rotating said x-ray source and said radiation detector with a rotational speed of at least 30°/s.

3. A method as claimed in claim 1 comprising administering said contrast agent to have a dwell time of at least four seconds in said examination region.

4. A method as claimed in claim 1 comprising administering said contrast agent to have a dwell time of at least five seconds in said examination region.

5. A method as claimed in claim 1 comprising obtaining said data at an image rate of twenty images per second.

6. A method as claimed in claim 1 comprising obtaining said data at an image rate of at least twenty-five images per second.

7. A method as claimed in claim 1 wherein said examination region contains a heart exhibiting a motion phase and comprising the additional steps of:

obtaining an electrocardiogram from said subject while obtaining said data; and based on said electrocardiogram, allocating at least one projection image in said plurality of projection images to said motion phase of said heart.

8. A method as claimed in claim 7 wherein said motion phase is the diastolic phase, and wherein the step of reconstructing a three-dimensional image comprises reconstructing said three-dimensional image exclusively from said at least one projection image allocated to said diastolic phase.

9. A method as claimed in claim 7 wherein the stop of obtaining said data comprises obtaining said data for a plurality of motion cycles of said heart, each of said motion cycles containing said motion phase, and wherein the step of reconstructing said three-dimensional image comprises employing respective projection images allocated to said motion phase in a plurality of said heart cycles for reconstructing said three-dimensional image, and computationally interpolating any missing projection images needed for a complete set of projection images for reconstructing said three-dimensional image.

10. A method as claimed in claim 7 wherein said heart exhibits a heart cycle containing said motion phase, and wherein the step of obtaining said data comprises obtaining data for a plurality of two-dimensional projection images within a predetermined time span in said heart cycle, and wherein the step of reconstructing said three-dimensional images comprises employing all of the projection images obtained within said predetermined time span for reconstructing said three-dimensional, and computationally interpolating any missing projection images needed for a complete set of projection images for reconstructing said three-dimensional image.

11. A method as claimed in claim 7 comprising the additional step of subdividing rotation of said x-ray source and said radiation detector into a plurality of equidistant projection angle ranges and wherein the step of reconstructing said three-dimensional image comprises selecting from each of said projection angle ranges a plurality of selected projection images that lie within a predetermined projection angular range and which have a minimum time interval from said motion phase dependent on said electrocardiogram, and using said selected projection images exclusively for reconstructing said three-dimensional image.

12. A method as claimed in claim 11 comprising overlapping said predetermined projection angle ranges to avoid motion-dependent unsteadiness in said three-dimensional image.

13. A method as claimed in claim 1 comprising employing a biplanar C-arm as said C-arm.

14. A medical examination apparatus for three-dimensional imaging of a moving examination subject comprising:

a contrast agent device for injecting a contrast agent into a subject, said contrast agent having a dwell time in an examination region of said subject;

a rotatable C-arm that exhibits mechanical instability at high rotational speeds;

an x-ray source, which emits an x-ray fan beam having a fan angle, and a radiation detector mounted on said C-arm for rotation by said C-arm around said examination region at least once through 180° plus said fan angle during said dwell time obtaining data during said dwell time representing a sufficient number of two-dimensional projections of said examination region to allow reconstruction of a three-dimensional image that is substantially free of artifacts due to said movement, said x-ray source and said radiation detector, due to said mechanical instability at said high speed, having respectively different geometric relations in different projections;

a device for recording anew the geometric relations of said x-ray source, said radiation detector and said subject for each of said projections as each of said projections is obtained; and an image reconstruction computer supplied with said data and the recorded geometric relations, for reconstructing a three-dimensional image from said data and for making said three-dimensional image free of said artifacts by using said recorded geometric relations.

15. A medical examination apparatus as claimed in claim 14 wherein said x-ray source and said radiation detector are mounted for rotation with a rotational speed of at least 30°/s.

16. A medical examination apparatus as claimed in claim 14 wherein said contrast agent device administers said contrast agent to have a dwell time of at least four seconds in said examination region.

17. A medical examination apparatus as claimed in claim 14 wherein said contrast agent device administers said contrast agent to have a dwell time of at least five seconds in said examination region.

18. A medical examination apparatus as claimed in claim 14 wherein said data are obtained at an image rate of at least twenty images per second.

19. A medical examination apparatus as claimed in claim 14 wherein said data are obtained at an image rate of at least twenty-five images per second.

20. A medical examination apparatus as claimed in claim 14 wherein said examination region contains a heart exhibiting a motion phase, and further comprises:

an ECG apparatus for obtaining an electrocardiogram from said subject while obtaining said data; and said computer, based on said electrocardiogram, allocating at least one projection image in said plurality of projection images to said motion phase of said heart.

21. A medical examination apparatus as claimed in claim 20 wherein said motion phase is the diastolic phase, and said computer reconstructs said three-dimensional image exclusively from said at least one projection image allocated to said diastolic phase.

22. A medical examination apparatus as claimed in claim 20 wherein said data are obtained for a plurality of motion cycles of said heart, each of said motion cycles containing said motion phase, and wherein said computer reconstructs said three-dimensional image employing respective projection images allocated to said motion phase in a plurality of said heart cycles, and computationally interpolates any missing projection images needed for a complete set of projection images for reconstructing said three-dimensional image.

23. A medical examination apparatus as claimed in claim 20 wherein said heart exhibits a heart cycle containing said motion phase, and wherein said data are obtained for a plurality of two-dimensional projection images within a predetermined time span in said heart cycle, and wherein said computer reconstructs said three-dimensional images employing all of the projection images obtained within said predetermined time span, and computationally interpolates any missing projection images needed for a complete set of projection images for reconstructing said three-dimensional image.

24. A medical examination apparatus as claimed in claim 20 wherein the rotation of said x-ray source and said radiation detector is subdivided into a plurality of equidistant projection angle ranges, and wherein said computer reconstructs said three-dimensional image by selecting, from each of said projection angle ranges, a plurality of selected projection images that lie within a predetermined projection angular range and which have a minimum time interval from sake motion phase dependent on said electrocardiogram, and uses said selected projection images exclusively for reconstructing said three-dimensional images.

25. A medical examination apparatus as claimed in claim 24 wherein said computer overlaps said predetermined projection angle ranges to avoid motion-dependent unsteadiness in said three-dimensional image.

26. A medical examination apparatus as claimed in claim 14 wherein said C-arm is a biplanar C-arm.

* * * * *